(12) United States Patent
Pathi et al.

(10) Patent No.: US 8,076,492 B2
(45) Date of Patent: Dec. 13, 2011

(54) PROCESS FOR PREPARING TRITYL OLMESARTAN MEDOXOMIL AND OLMESARTAN MEDOXOMIL

(75) Inventors: Srinivas Laxminarayan Pathi, Karnataka (IN); Ravikumar Puppala, Banaswadi (IN); Rajendra Narayanrao Kankan, Mumbai (IN); Dharmaraj Ramachandra Rao, Mumbai (IN)

(73) Assignee: Cipla Limited, Mumbai (IN)

( * ) Notice: Subject to any disclaimer, the term of this patent is extended or adjusted under 35 U.S.C. 154(b) by 69 days.

(21) Appl. No.: 12/444,502

(22) PCT Filed: Oct. 9, 2007

(86) PCT No.: PCT/GB2007/003821
§ 371 (c)(1),
(2), (4) Date: Aug. 20, 2009

(87) PCT Pub. No.: WO2008/043996
PCT Pub. Date: Apr. 17, 2008

(65) Prior Publication Data
US 2010/0160643 A1 Jun. 24, 2010

(30) Foreign Application Priority Data
Oct. 9, 2006 (IN) .................. 1663/MUM/2006

(51) Int. Cl.
*C07D 233/00* (2006.01)
*C07D 257/04* (2006.01)
*C07D 405/14* (2006.01)
(52) U.S. Cl. ...................... 548/250; 548/253
(58) Field of Classification Search .............. 548/250, 548/253
See application file for complete search history.

(56) References Cited

U.S. PATENT DOCUMENTS
5,616,599 A 4/1997 Yanagisawa et al.
2009/0131680 A1* 5/2009 Zupancic et al. ............ 548/253

FOREIGN PATENT DOCUMENTS
WO 2004085428 A1 10/2004
WO 2008043996 A2 4/2008
WO 2008043996 A3 4/2008

OTHER PUBLICATIONS

Yu, Xin-Hong, et al., "Synthesis of a novel angiotensin II receptor antagonist olmesartan medoxomil," XP009093461, Zpril 2005, pp. 189-192, vol. 31, No. 2, J. East China Univ. Sci & Tech. (Also see IDS filed May 20, 2009, NPL cite #3).*

Foreign Communication from a related counterpart application—International Preliminary Report on Patentability, PCT/GB2007/003821, Feb. 27, 2009, 10 pages.
Foreign Communication from a related counterpart application—International Search Report and Written Opinion, PCT/GB2007/003821, Aug. 13, 2008, 12 pages.
Yu, Xin-Hong, et al., "Synthesis of a novel angiotensin II receptor antagonist olmesartan medoxomil," XP009093461, Apr. 2005, pp. 189-192, vol. 31, No. 2, Journal of East China University of Science and Technology (Natural Science Edition).

* cited by examiner

*Primary Examiner* — Susannah Chung
(74) *Attorney, Agent, or Firm* — Conley Rose, P.C.; Rodney B. Carroll

(57) ABSTRACT

A process for the preparation of trityl olmesartan comprising (a) condensing 4-(1-hydroxy-1-methylethyl)-2-propyl-imidazol-5-carboxylic acid alkyl ester with trityl biphenyl bromide in the presence of a polar aprotic solvent and a base selected from the group consisting of alkali metal carbonates, alkali metal hydroxides, alkali metal alkoxides, and tertiary amines to obtain a compound of formula V,

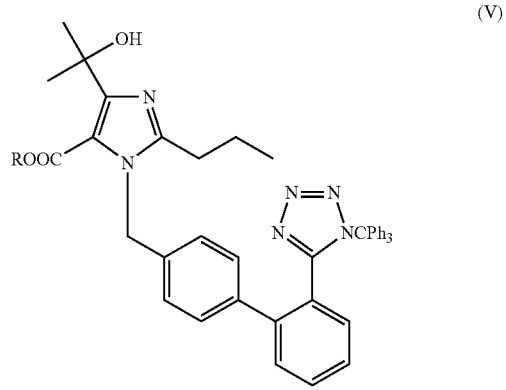

(V)

b) deesterifying the compound of formula (V) with a base; and c) reacting the product of step (b) with 4-halomethyl-5-methyl-2-oxo-1,3-dioxolene of formula (IV),

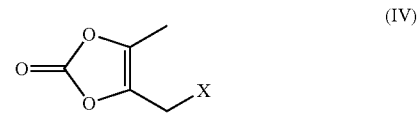

(IV)

wherein X is halogen selected from F or Cl or Br or I, to obtain trityl olmesartan medoxomil of formula. The trityl olmesartan medoxomil may be deprotected to produce olmesartan medoxomil.

28 Claims, No Drawings

PROCESS FOR PREPARING TRITYL OLMESARTAN MEDOXOMIL AND OLMESARTAN MEDOXOMIL

CROSS-REFERENCE TO RELATED APPLICATIONS

This application is a filing under 35 U.S.C. 371 of International Application No. PCT/GB2007/003821 filed Oct. 9, 2007, entitled "Process for Preparing Trityl Olmesartan Medoxomil and Olmesartan Medoxomil," claiming priority of Indian Patent Application No. 1663/MUM/2006 filed Oct. 9, 2006, which applications are incorporated by reference herein in their entirety.

FIELD OF INVENTION

The present invention relates to an improved process for the synthesis of trityl olmesartan medoxomil and olmesartan medoxomil.

BACKGROUND OF THE INVENTION

Olmesartan medoxomil is a prodrug that is hydrolysed to olmesartan during absorption from the gastrointestinal tract. Olmesartan is a selective AT1 type angiotensin II receptor antagonist, which is by virtue of its pharmacological properties, particularly useful in the treatment of hypertension. The chemical name for olmesartan medoxomil is 4-(1-hydroxy-1-methylethyl)-2-propyl-1-[[2-(1H-tetrazol-5-yl) [1,1-biphenyl]-4-yl]methyl]-1H-imidazole-5-carboxylic acid (5-methyl-2-oxo-1,3-dioxol-4-yl)methyl ester, and is represented by the following structure (formula I).

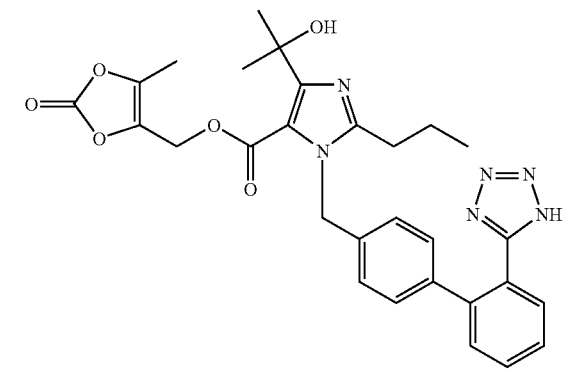

Formula I

Olmesartan medoxomil was first disclosed in U.S. Pat. No. 5,616,599. The synthetic method employed is depicted in the following reaction Scheme 1, where an imidazole derivative is condensed with a dioxolyl compound, then reacted with a substituted biphenyl methyl halide to obtain trityl olmesartan medoxomil which is then deprotected to obtain crude olmesartan medoxomil.

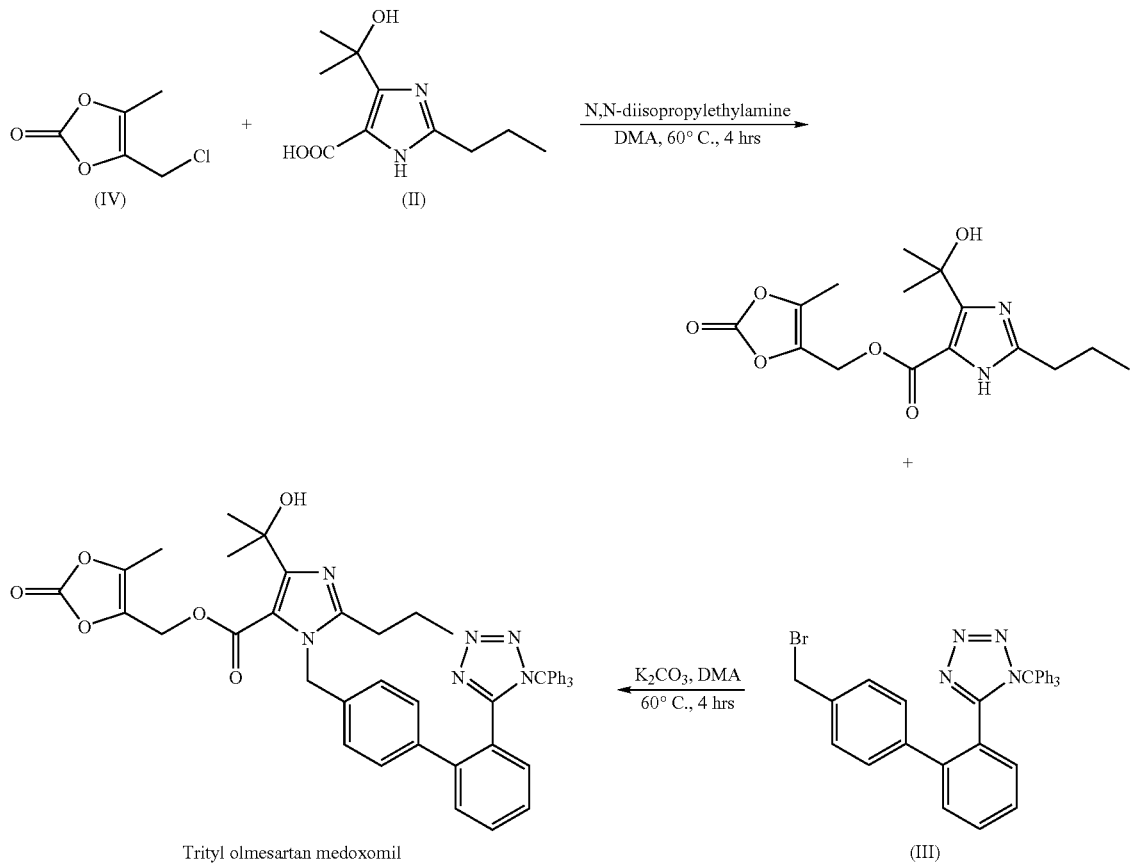

Scheme 1

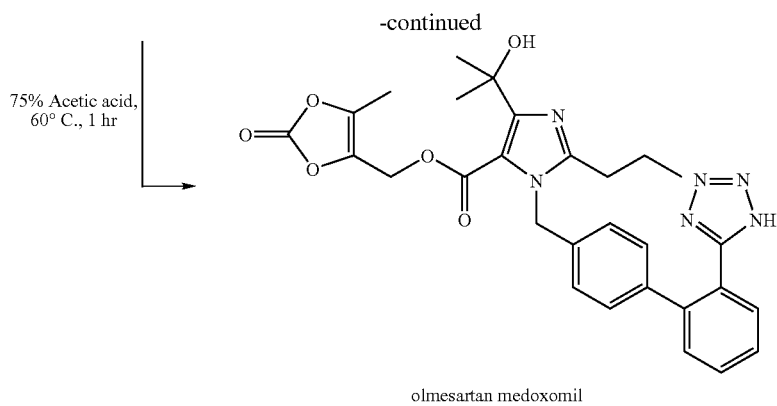

olmesartan medoxomil

The '599 patent also discloses a process for preparing olmesartan medoxomil in examples 18(a) and 78. The process focuses on the coupling reaction between the imidazole derivative and the substituted biphenyl methyl halide, the condensation with the dioxolyl compound and the subsequent deprotection to isolate crude olmesartan medoxomil. Example 18(a) describes the coupling reaction which involves the use of a strong base (sodium hydride). Such strong bases are hazardous and difficult to handle on an industrial scale. The coupling reaction is conducted at a temperature of 60° C. The reaction conditions in the coupling step are such that impurities are formed which require the coupled intermediate to be isolated and purified. More specifically, the coupled intermediate is isolated as a residue which requires purification by column chromatography. The chromatographed product undergoes further isolation steps involving crystallisation in diisopropyl ether. The yield of ethyl 4-(1-hydroxy-1-methylethyl)-2-propyl-1-{4-[2-(trityltetrazol-5-yl)phenyl]phenyl}methyl imidazole-5-carboxylate prepared according to example 18(a) is 238.4% w/w. In example 78(a), the product of example 18 is used to produce lithium 4-(1-hydroxy-1-methylethyl)-2-propyl-1-{4-[2-(trityltetrazol-5-yl)phenyl]phenyl}-methylimidazole-5-carboxylate. The yield of trityl olmesartan medoxomil prepared according to the process in example 78 is 97.6% w/w. The overall yield of the example 18(a) and example 78 processes is 230% w/w. The overall process is hazardous, tedious, time consuming and involves many steps, including isolation steps.

WO 2004/085428 describes a process for the preparation of olmesartan medoxomil which comprises: a) ring opening the 4,4-dimethyl-2-propyl-1-[4-{2-(triphenyl methyltetrazole-5-yl)phenyl}phenyl]methyl-4,6-dihydrofuran[3,4-d]imidazole-6-one; b) condensing the resulting 4-(1-hydroxy-1-methylethyl)-2-propyl-1-[4-{2-(triphenylmethyltetrazole-5-yl)phenyl}phenyl]methylimidazole-5-carboxylic acid with 4-halomethyl-5-methyl-oxo-1,3-dioxyheterocyclopentene in the presence of alkali; followed by c) deprotection to obtain olmesartan medoxomil.

There is ample literature available on the deprotection of trityl olmesartan medoxomil and purification of olmesartan medoxomil. There are also several other processes reported in the prior art for the preparation of olmesatan medoxomil and its intermediates.

The synthesis of olmesartan described in the prior art involves multiple reaction steps, each requiring different conditions, solvents, temperature, etc. This necessitates a discontinuous process and more than one isolation step, which entail longer processing time, lower yields (as product is lost during each isolation step), increased effluent load and increased solvent usage, in comparison with a continuous process. Hence, there is a constant need to develop more efficient and economical synthetic routes suitable for industrial scale up.

The present inventors have now found a way of synthesizing trityl olmesartan medoxomil and olmesartan medoxomil which avoids the multiple isolation steps used in the previously described processes.

SUMMARY OF THE INVENTION

The object of the present invention is to provide an improved process for the synthesis of olmesartan medoxomil, which is economical and suitable for industrial application and is eco or environmentally friendly.

Another objective of the present invention is to provide a synthesis of trityl olmesartan medoxomil in a single reaction vessel, followed by isolation of the product, which can be further detritylated to give olmesartan medoxomil.

Another object of the invention is to provide a one-pot process for the synthesis of olmesartan medoxomil which is carried out without isolating the reaction intermediates thereby avoiding the use of multiple vessels, large quantity of solvents and additional process steps, thus making the process cost effective.

In accordance with the above objectives, the present invention provides a cost effective synthesis of highly pure olmesartan medoxomil.

The synthesis involves an initial coupling of a 4-(1-hydroxy-1-methylethyl)-2-propyl-imidazol-5-carboxylic acid alkyl ester with a trityl biphenyl halide using conditions that minimise the formation of impurities. The product of the coupling reaction is pure enough to be used in the subsequent synthesis of olmesartan medoxomil without the need for isolation and purification of the coupled product, or of intermediates formed in the subsequent synthesis to prepare olmesartan medoxomil.

In the context of the present invention, the term "one-pot" is intended to mean that the steps referred to are carried out in a single reaction vessel. In the context of the present invention, the term "isolated" is intended to mean that the product/intermediate referred to is not separated as a solid. Thus, the various steps may be carried out in more than one reaction vessel but the intermediate(s) are not necessarily isolated. Alternatively, all the steps may be carried out in a single reaction vessel and none of the intermediates is isolated.

According to a first aspect of the present invention, there is provided a process for the preparation of trityl olmesartan of formula (VI),

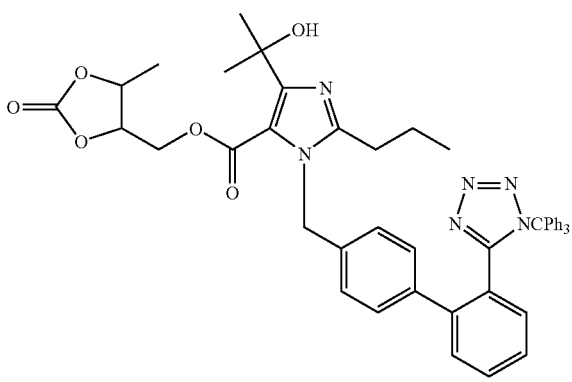

comprising (a) condensing 4-(1-hydroxy-1-methylethyl)-2-propyl-imidazol-5-carboxylic acid alkyl ester of formula (II),

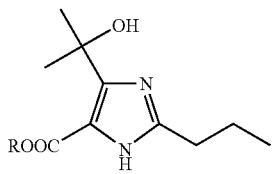

wherein R is $C_1$-$C_6$ alkyl with trityl biphenyl bromide of formula (III),

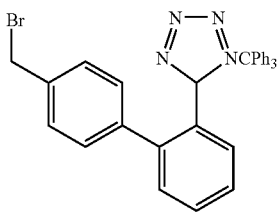

in the presence of a polar aprotic solvent and a base selected from the group consisting of alkali metal carbonates, alkali metal hydroxides, alkali metal alkoxides, and tertiary amines to obtain a compound of formula V,

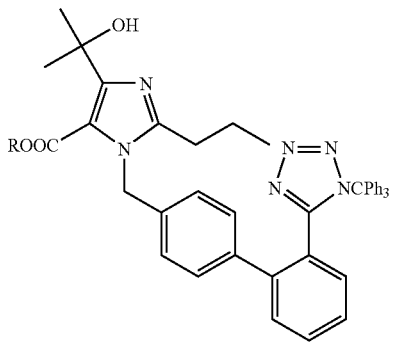

b) deesterifying the compound of formula (V) with a base; and c) reacting the product of step (b) with 4-halomethyl-5-methyl-2-oxo-1,3-dioxolene of formula (IV),

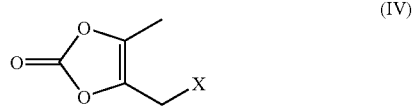

wherein X is halogen selected from F or Cl or Br or I, to obtain trityl olmesartan medoxomil of formula (VI).

The process is carried out in the presence of a mild base, such as alkali metal carbonates, alkali metal hydroxides, alkali metal alkoxides, and tertiary amines. The prior art processes, for example Example 18(a) of U.S. Pat. No. '599, are carried out in the presence of stronger bases, such as sodium hydride. It has surprisingly been discovered that the use of a mild base leads to the formation of fewer impurities. Thus, there is no need for intermediates in the process to be isolated and purified before being used in the next reactive step. Suitably, the alkali metal carbonate is potassium carbonate. Optionally, the alkali metal hydroxide is sodium hydroxide or potassium hydroxide, preferably sodium hydroxide.

It will be appreciated that other trityl biphenyl halides may be used in the process of the present invention, for example trityl biphenyl chloride and trityl biphenyl iodide.

In an embodiment, R is a straight or branched chain $C_1$ to $C_6$ alkyl group. For example, R' may be ethyl, n-propyl, isopropyl, n-butyl, isobutyl, t-butyl, n-pentyl, n-hexyl or the like. Preferably, R is ethyl.

In an embodiment, the polar aprotic solvent in step (a) is selected from the group consisting of acetone, tetrahydrofuran, methyl ethyl ketone, acetonitrile, ethyl acetate, dimethyl formamide, dimethyl acetamide, dimethyl sulfoxide and mixtures thereof. Preferably, the polar aprotic solvent is dimethyl acetamide.

It has also surprisingly been found that the temperature of the reaction mixture in step (a) can affect the formation of impurities. The step (a) process may be carried out at a temperature ranging from 40° C. to 55° C., preferably 40° C. to 50° C., most preferably 45° C. to 50° C. The prior art processes, for example Example 18(a) are carried out at higher temperatures, for example 60° C.

The base used in step (b) may be selected from the group consisting of inorganic bases and organic bases. For example, the inorganic base is selected from the group consisting of alkali metal hydroxides, alkali metal carbonates and alkali metal alkoxides. Suitably, the alkali metal carbonate is potassium carbonate. Optionally, the alkali metal hydroxide is sodium hydroxide or potassium hydroxide, preferably sodium hydroxide. Suitably, the organic base is a tertiary amine.

If necessary, following the coupling in step (c), the reaction mass is neutralized with a suitable acid to obtain trityl olmesartan medoxomil (formula (VI)). The acid may be selected from the group consisting of carboxylic acids and inorganic acids. In an embodiment, the carboxylic acid is formic acid or acetic acid, preferably acetic acid. In another embodiment, the inorganic acid is hydrochloric acid, hydrobromic acid or sulfuric acid, preferably hydrochloric acid.

In an embodiment, steps (a), (b) and (c) are carried out in a single reaction vessel.

In another embodiment, neither one of the products of steps (a) or (b) is isolated.

According to another aspect of the present invention, there is provided a process for the preparation of olmesartan medoxomil of formula I,

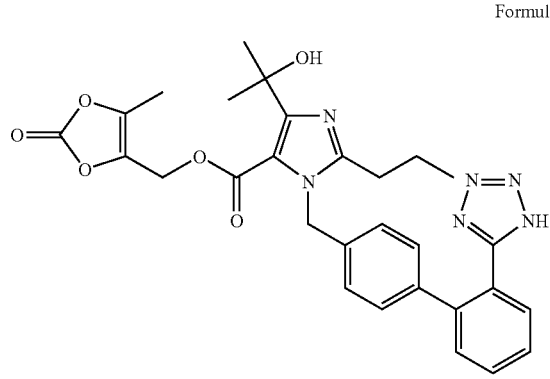

Formula I comprising preparing trityl olmesartan medoxomil of formula (VI) according to the process described above and d) deprotecting the trityl olmesartan medoxomil (VI) to yield olmesartan medoxomil (I). The overall yield of this process is 240% w/w.

In an embodiment, steps (a), (b), (c) and (d) are carried out in a single reaction vessel.

In another embodiment, steps (a), (b) and (c) are carried out in a single reaction vessel. The trityl olmesartan medoxomil of formula (VI) may be isolated prior to deprotection in step (d). The isolated trityl olmesartan medoxomil of formula (VI) may be purified prior to deprotection in step (d).

In an embodiment, neither one of the products of steps (a) or (b) is isolated as a solid.

In a further embodiment, none of the products of steps (a), (b) or (c) is isolated as a solid.

Deprotection of the trityl olmesartan medoxomil may be carried out according to any conventional method.

In an embodiment, the deprotection is carried out in the presence of an acid. Suitable acids are selected from the group consisting of organic carboxylic acids, sulfonic acids, and inorganic acids. The organic carboxylic acid may be formic acid, oxalic acid, acetic acid, trimethyl acetic acid or trifluoroacetic acid, preferably acetic acid. The sulfonic acid may be methanesulfonic acid or p-toluene sulfonic acid. The inorganic acid may be hydrochloric acid, hydrobromic acid, sulfuric acid, pivalic acid or phosphoric acid, preferably hydrochloric acid.

According to another aspect of the present invention, there is provided a process for the preparation of a compound of formula (V),

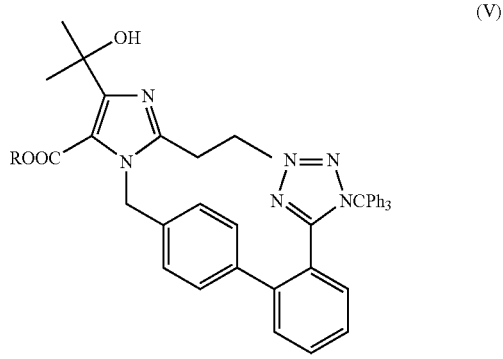

(V)

comprising condensing 4-(1-hydroxy-1-methylethyl)-2-propyl-imidazol-5-carboxylic acid alkyl ester of formula (II),

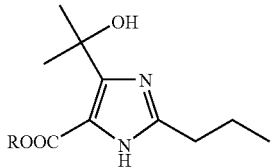

(II)

wherein R is $C_1$-$C_6$ alkyl with trityl biphenyl bromide of formula (III),

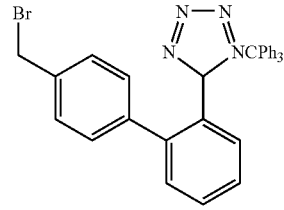

(III)

in the presence of a polar aprotic solvent and a base selected from the group consisting of alkali metal carbonates, alkali metal hydroxides, alkali metal alkoxides, and tertiary amines to obtain the compound of formula V. The product of this coupling reaction may be used to produce trityl olmesartan medoxomil and olmesartan medoxomil according to any conventional method. The product of the coupling reaction need not be isolated before being subjected to further steps to produce trityl olmesartan medoxomil or olmesartan medoxomil.

The above process steps are carried out conveniently in a single pot without changing the reaction vessel.

DETAILED DESCRIPTION OF THE INVENTION

The invention will now be described in detail in connection with certain preferred and optional embodiments, so that various aspects thereof may be more fully understood and appreciated.

The present invention describes a more practical, economical and efficient synthesis for the preparation of highly pure trityl olmesartan medoxomil and olmesartan medoxomil. This process is particularly advantageous in comparison with known methods because the reaction is carried out without isolating the intermediates formed by the preceding step, thus reducing the impurity formed and increasing yield and purity of the product. The process of the present invention eliminates the risk of handling hazardous chemicals, reduces enhanced cost associated with multiple reactors, and reduces reaction time and cleanup, thus making the process more economical and industrially viable.

In an embodiment, the present invention provides a method of synthesizing olmesartan medoxomil, which comprises: (a) condensing 4-(1-hydroxy-1-methylethyl)-2-propyl imidazol-5-carboxylic acid alkyl ester of formula (II) where R is $C_1$-$C_6$ alkyl, with trityl biphenyl bromide of formula (III) in the presence of a polar aprotic solvent and a mild base to obtain a compound of formula V (a first intermediate),

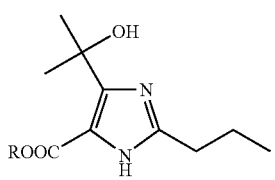

(II)

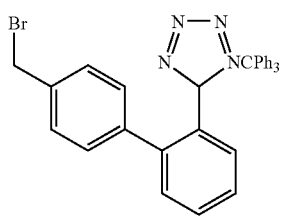

(III)

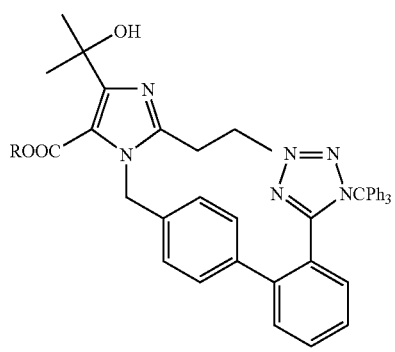

(V)

(b) deesterifying the resulting intermediate (V) of step (a) to obtain a third intermediate;

(c) reacting the product of step (b) with 4-halomethyl-5-methyl-2-oxo-1,3-dioxolene of formula (IV) to obtain trityl olmesartan medoxomil (a third intermediate) of formula VI;

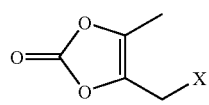

(IV)

wherein X = F or Cl or Br or I (VI)

and (d) deprotecting the trityl olmesartan medoxomil (VI) to yield olmesartan medoxomil.

In a most preferred embodiment, steps (a), (b), (c) and optionally (d) are carried out in a single reaction vessel and without isolating the intermediates formed.

In an embodiment, the process of the present invention for preparing olmesartan medoxomil may also be depicted as in Scheme 2.

Scheme 2

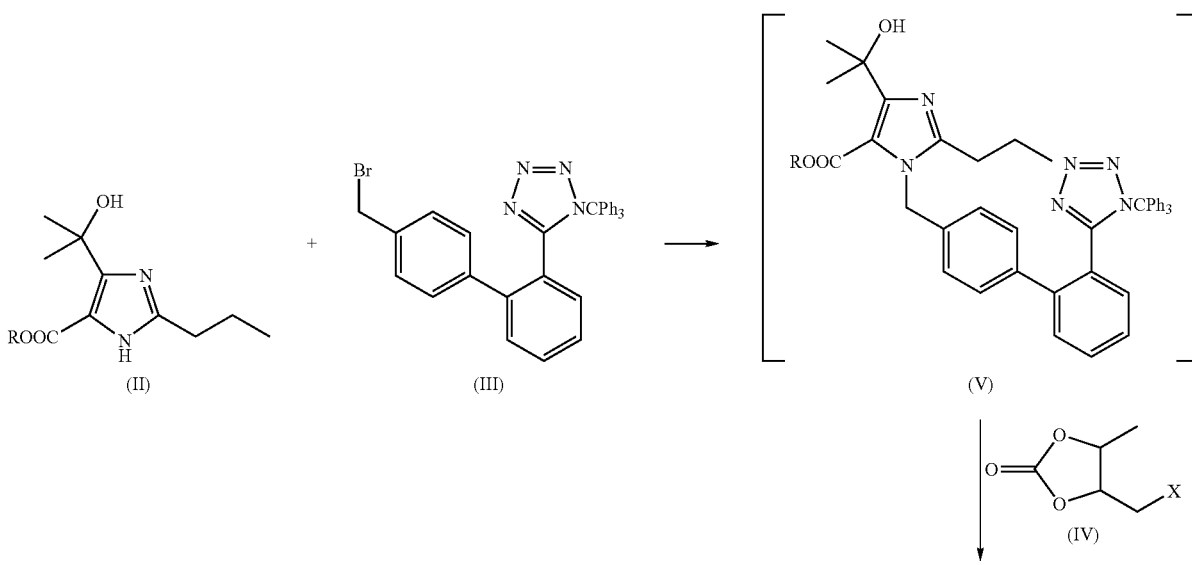

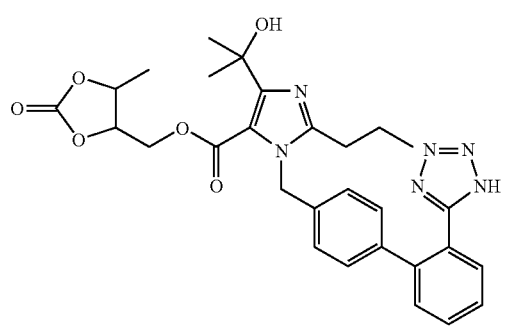

Olmesartan medoxomil
(I)

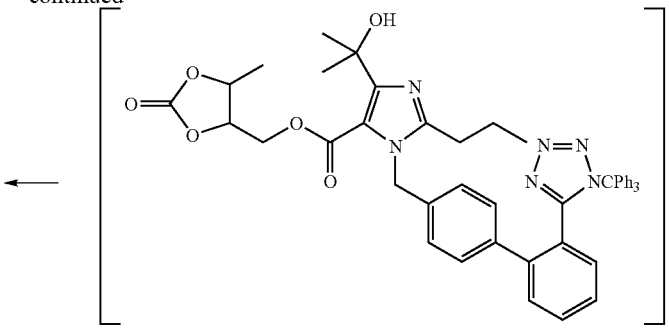

Trityl olmesartan medoxomil
(VI)

[Brackets indicate intermediates that could be isolated but are not isolated in the integrated process].

The overall synthetic process for the preparation of olmesartan medoxomil of the present invention comprises steps (a), (b), (c) and (d) that may all be carried out in a single reaction vessel.

In step (a), 4-(1-hydroxy-1-methylethyl)-2-propyl imidazol-5-carboxylic acid alkyl ester of formula (II) is reacted with trityl biphenyl bromide of formula (III) in the presence of a polar aprotic solvent and a mild base to yield the corresponding alkyl-4-(1-hydroxy-1-methylethyl)-2-propyl1-{4-[2-(trityltetazol-5-yl)phenyl]phenyl}-methylimidazol carboxylate of formula V (intermediate 1), wherein R is an alkyl group selected from $C_1$ to $C_6$ alkyl group, preferably an ethyl group.

The polar aprotic solvents used in step a) of the process may be selected from acetone, tetrahydrofuran, methyl ethyl ketone, acetonitrile, ethyl acetate, dimethyl formamide, dimethyl acetamide, dimethyl sulfoxide, or mixtures thereof, preferably dimethyl formamide or dimethyl acetamide.

Preferred bases for use in step a) include inorganic bases such as alkali metal carbonates such as potassium carbonate, alkali metal hydroxides such as sodium hydroxide or potassium hydroxide, alkali metal alkoxides or organic bases such as tertiary amines.

The process is carried out at a temperature ranging from 25 to 30° C. or from 25° C. to an elevated temperature such as the reflux temperature of the solvent used, preferably at a temperature ranging from 40 to 65° C. In a particularly preferred embodiment, step (a) is carried out at a temperature ranging from 40 to 65° C., more preferably at 40° C. to 50° C., most preferably at a temperature ranging from 45° C. to 50° C.

The product of step (a) is preferably not isolated before being subjected to step (b). In other words, the product of step (a) is used directly for the reaction in step (b). In step (b), deesterification of the compound of formula V (intermediate 1) may be carried out using a suitable base. Suitable bases include various inorganic bases such as alkali metal hydroxides, alkali metal carbonates, or alkali metal alkoxides. Alternatively, suitable bases include organic bases such as tertiary amines. Preferably, the base is potassium tertiary butoxide or diisopropylethyl amine.

The product of step (b) is preferably not isolated before being subjected to the reaction of step (c). In other words, the product of step (b) is used directly for the reaction in step (c). In step (c) the product of step (b), is condensed with 4-halomethyl-5-methyl-2-oxo-1,3-dioxolene of formula (IV), wherein X is halogen selected from bromo, chloro, iodo and fluoro, preferably bromo. The reaction mass may then be neutralized with a suitable acid to obtain trityl olmesartan medoxomil of formula VI (intermediate 3, which may not be isolated). The acid used for neutralization may be selected from carboxylic acids for example formic acid, acetic acid or inorganic acids such as hydrochloric acid, hydrobromic acid or sulfuric acid.

The product of step (c) may or may not be isolated before being subjected to step (d). In other words, the product of step (c) may be used directly for the detritylation reaction in step (d) or may be isolated before detritylation. If the product of step (c) is isolated, it may be purified prior to detritylation.

The reaction mass containing trityl olmesartan medoxomil may be treated with an appropriate acid which is selected from organic carboxylic acids, sulfonic acids, inorganic acids or mixtures thereof. Organic carboxylic acids may include formic acid, oxalic acid, acetic acid, trimethyl acetic acid or trifluoroacetic acid. Sulfonic acids may include methanesulfonic acid or p-toluene sulfonic acid. Inorganic acids may include hydrochloric acid, hydrobromic acid, sulfuric acid, pivalic acid or phosphoric acid, preferably hydrochloric acid or acetic acid. The pH of the reaction mass may be neutralized with organic or inorganic bases. Olmesartan medoxomil is then isolated from the reaction mixture by conventional means. If required it may be further purified from a suitable solvent or solvent mixture.

In another aspect of the present invention, trityl olmesartan medoxomil is prepared in a single reaction vessel as described above and isolated, for example by quenching in water. The crude trityl olmesartan medoxomil can be purified further from a suitable solvent or solvent mixture.

The trityl olmesartan medoxomil is then deprotected by any conventional method or any of the methods described above to yield olmesartan medoxomil.

EXAMPLES

The following examples, which include preferred embodiments, illustrate the practice of this invention, it being understood that the particulars shown are by way of example and for purpose of illustrative discussion of preferred embodiments of the invention.

Example 1

Preparation of Olmesartan Medoxomil

To dimethyl acetamide (300 ml) was added 4-(1-hydroxy-1-methylethyl)-2-propyl imidazol-5-carboxylic acid ethyl ester (50 gms) and powdered sodium hydroxide (26 gms). To this, 4-[2-(trityltetrazol-5-yl)phenyl]benzyl bromide (135 gms) was charged at 45-50° C. The contents were stirred for 5 hours at 45-50° C. Diisopropylethyl amine (100 ml) was charged to the reaction mass at 40-45° C. A solution of 5-methyl-2-oxo-1,3-dioxane-4-yl)methyl chloride (80 gms) diluted with dimethyl acetamide (160 ml) was slowly added to the reaction mass at 40-45° C. over a period of 1 hour. The contents were heated to 60-65° C. and maintained for 4 hours. The reaction mass was then cooled to 30-35° C. and neutralized with concentrated hydrochloride acid. The reaction mass was filtered to remove inorganic impurities, charcoalized using charcoal (10 gms) and stirred for 30 minutes at 40-45° C. The reaction mass was filtered over hyflo. The clear filtrate was acidified with hydrochloric acid (100 ml) slowly at 25-30° C. The contents were stirred at 60° C. for 1 hour. The reaction mass was chilled to 0-5° C. and filtered to remove tritanol. The reaction mass was concentrated under reduced pressure. The residue was quenched with water (500 ml), neutralized with base and extracted in dichloromethane (500 ml). The clear dichloromethane extract was then concentrated under reduced pressure and stripped off with acetone. The residue thus obtained was isolated from acetone (250 ml) to give 55 gms of the title compound. Chromatographic purity->99%.

Example 2

Preparation of Olmesartan Medoxomil

To dimethyl acetamide (600 ml) was added 4-(1-hydroxy-1-methylethyl)-2-propyl imidazol-5-carboxylic acid ethyl ester (100 gms) and powdered potassium hydroxide (50 gms). To this was charged 4-[2-(trityltetrazol-5-yl)phenyl]benzyl bromide (270 gms) at 45-50° C. The contents were stirred for 5 hours at 45-50° C. Diisopropylethyl amine (200 ml) was charged to the reaction mass at 40-45° C. To this was slowly added a solution of 5-methyl-2-oxo-1,3-dioxane-4-yl)methyl chloride (160 gms) diluted with dimethyl acetamide (320 ml) at 40-45° C. over a period of 1 hour. The contents were heated to 60-65° C. and maintained for 4 hours. The reaction mass was then cooled to 30-35° C. and was neutralized with concentrated hydrochloride acid. The reaction mass was filtered to remove inorganic impurities. The reaction mass was charcoalized using charcoal (20 gms) and was stirred for 30 minutes at 40-45° C. The reaction mass was filtered over hyflo. The clear filtrate was acidified with hydrochloric acid (200 ml) slowly at 25-30° C. The contents were stirred at 60° C. for 1 hour. The reaction mass was chilled to 0-5° C. and was filtered to remove tritanol. The reaction mass was concentrated under reduced pressure. The residue was quenched with water (1000 ml), neutralized with base and extracted in dichloromethane (1000 ml). The clear dichloromethane extract was then concentrated under reduced pressure, stripped off with acetone. The residue thus obtained was isolated from the acetone (500 ml) to give 110 gms of the title compound. Chromatographic purity->99%.

Example 3

Preparation of Olmesartan Medoxomil

To dimethyl acetamide (800 ml) was added 4-(1-hydroxy-1-methylethyl)-2-propyl imidazol-5-carboxylic acid ethyl ester (100 gms) and powdered potassium carbonate (200 gms). To this was charged 4-[2-(trityltetrazol-5-yl)phenyl]benzyl bromide (300 gms) at 45-50° C. The contents were stirred for 8-10 hours at 45-50° C. The insolubles were filtered. The contents were cooled to 5-10° C. Potassium tertiary butoxide (100 gms) was charged at a temperature below 45° C. The reaction was maintained at 40-45° C. for 3 hrs. To this was slowly added 5-methyl-2-oxo-1,3-dioxane-4-yl)methyl chloride at 40-45° C. over a period of 1 hour. The contents were heated to 60-65° C. and maintained for 4 hours. The reaction mass was then cooled to 30-35° C. and was neutralized with concentrated hydrochloride acid. The reaction mass was filtered to remove inorganics. The reaction mass was charcoalized using charcoal (10 gms) and was stirred for 30 minutes at 40-45° C. The reaction mass was filtered over hyflo. The clear filtrate was acidified with hydrochloric acid (100 ml) slowly at 25-30° C. The contents were stirred at 60° C. for 1 hour. The reaction mass was chilled to 0-5° C. and was filtered to remove tritanol. The reaction mass was concentrated under reduced pressure. The residue was quenched with water (500 ml), neutralized with base and extracted in dichloromethane (500 ml). The clear dichloromethane extract was then concentrated under reduced pressure, stripped off with acetone. The residue thus obtained was isolated from the acetone (250 ml) to give 55 gms of the title compound. Chromatographic purity->99%.

In examples 1 to 3, filtration steps are involved, but the intermediates in the process are not isolated as solids. The filtration steps are used to remove insoluble by-products and impurities; the intermediates remain in solution as the filtrate. The olmesartan medoxomil is isolated as a solid in the final step. These examples exemplify the embodiment in which none of the intermediates (first, second or third) is isolated.

Example 4

Preparation of Trityl Olmesartan Medoxomil

To dimethyl acetamide (300 ml) was added 4-(1-hydroxy-1-methylethyl)-2-propyl imidazol-5-carboxylic acid ethyl ester (50 gms) and powdered potassium hydroxide (25 gms). To this was charged 4-[2-(trityltetrazol-5-yl)phenyl]benzyl bromide (135 gms) at 45-50° C. The contents were stirred for 5 hours at 45-50° C. Diisopropylethyl amine (100 ml) was charged to the reaction mass at 40-45° C. To this was slowly added a solution of 5-methyl-2-oxo-1,3-dioxane-4-yl)methyl chloride (80 gms) diluted with dimethyl acetamide (160 ml) at 40-45° C. over a period of 1 hour. The contents were heated to 60-65° C. and maintained for 4 hours. The reaction mass was then cooled to 30-35° C. and was neutralized with concentrated hydrochloride acid. The reaction mass was filtered to remove inorganics. The reaction mass was charcoalized using charcoal (10 gms) and was stirred for 30 minutes at 40-45° C. The reaction mass was filtered over hyflo. The clear filtrate was quenched with purified water (200 ml) at 25-30° C. over a period of 3-4 hours. The contents were stirred at 25-30° C. for 30 minutes. Crude trityl olmesartan medoxomil was isolated by filtration, slurried in water (500 ml), centrifuged and dried under reduced pressure at 45-50° C.

Example 5

Preparation of Trityl Olmesartan Medoxomil

To dimethyl sulphoxide (800 ml), sodium hydroxide powder (50 gms) was added under nitrogen atmosphere and stirred at 20-25° C. for 10 minutes. To this, 4-(1-hydroxy-1-methylethyl)-2-propyl-imidazole-5-ethyl carboxylate (100 gms) was added at 20-25° C. 5-(4'-bromomethyl-biphenyl)-2-yl-1-trityl tetrazole (270 gms) was added slowly at 20-25° C., and the reaction mass was stirred at 20-25° C. for 12 hours. Further 10% sodium hydroxide solution (100 ml) was added to the reaction mass at 20-25° C. The temperature of the reaction mass was raised to 40-45° C., the contents stirred at 40-45° C. for 2 hours and 5-methyl-2-oxo-1,3-dioxane-4-yl) methyl chloride (160 gms) was added slowly at 45-50° C. over a period of 45 minutes. The contents were stirred at 45-50° C. for 2 hours. The reaction mass was then cooled to 0-5° C., stirred for 1 hour at 0-5° C., filtered and slurried in water (1.0 lt) at 40-45° C. for 1 hour, filtered at 40° C. and dried at 40° C. To the dried material, ethyl acetate (2.5 lt) was added, heated to 50-55° C. for complete dissolution, ethyl acetate was distilled off to 1.0 lt stage under vacuum at 45-50° C. The contents were cooled to 0-5° C., stirred at 0-5° C. for 3 hours, filtered, washed with chilled methanol (100 ml) and dried under vacuum at 40-45° C. to give 250 gms of the title compound. Purity by HPLC: >99%.

In examples 4 and 5, filtration steps are involved, but the first and second intermediates in the process are not isolated as solids. The filtration steps are used to remove insoluble by-products and impurities; the intermediates remain in solution as the filtrate. The trityl olmesartan medoxomil is isolated as a solid in the final step. These examples exemplify the embodiment in which neither one of the first or second intermediates is isolated. The isolated trityl olmesartan medoxomil is taken on for purification, as exemplified in example 6.

Example 6

Purification

Crude trityl olmesartan medoxomil (140 gms) was dissolved in 1120 ml of ethyl acetate, distilled up to 560 ml and chilled to 0-5° C. Isopropyl acetate (70 ml) and methanol (35 ml) were charged to the reaction mass. The contents were stirred at 0-5° C. for 30 minutes. Pure trityl olmesartan medoxomil was isolated by filtration and was dried under reduced pressure at 45-50° C. to give 110 gms of the title compound. Purity by HPLC->99%.

Example 7

Preparation of Olmesartan Medoxomil

To 75% aqueous acetic acid (1000 ml) was slowly added trityl olmesartan medoxomil (110 gms) [prepared as described in example 5] at 25-30° C. The contents were stirred at 60° C. for 1 hour. The reaction mass was chilled to 0-5° C. and filtered to remove tritanol. The reaction mass was concentrated under reduced pressure. The residue was quenched with water (500 ml), neutralized with a base and extracted in dichloromethane (500 ml). The clear dichloromethane extract was then concentrated under reduced pressure and stripped off with acetone. The residue thus obtained was isolated from the acetone (250 ml) to give 55 gms of the title compound. Chromatographic purity->99%.

It will be appreciated that the invention may be modified within the scope of the appended claims.

What is claimed is:
1. A process for the preparation of trityl olmesartan medoxomil of formula (VI):

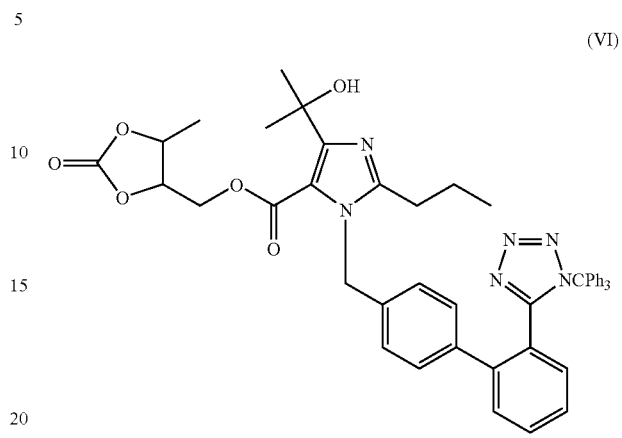

(VI)

comprising (a) condensing 4-(1-hydroxy-1-methylethyl)-2-propyl-imidazol-5-carboxylic acid alkyl ester of formula (II):

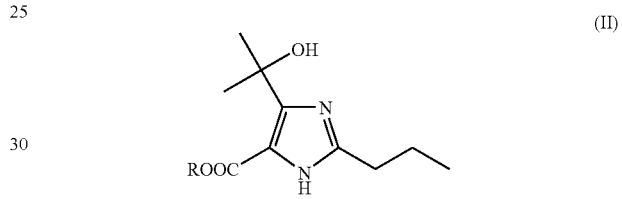

(II)

wherein R is $C_1$-$C_6$ alkyl with trityl biphenyl bromide of formula (III):

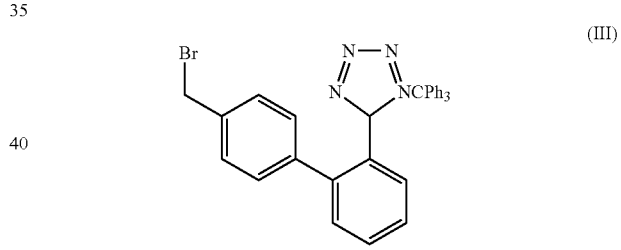

(III)

in the presence of a polar aprotic solvent and a base selected from the group consisting of alkali metal carbonates, alkali metal hydroxides, alkali metal alkoxides, and tertiary amines to obtain a compound of formula (V),

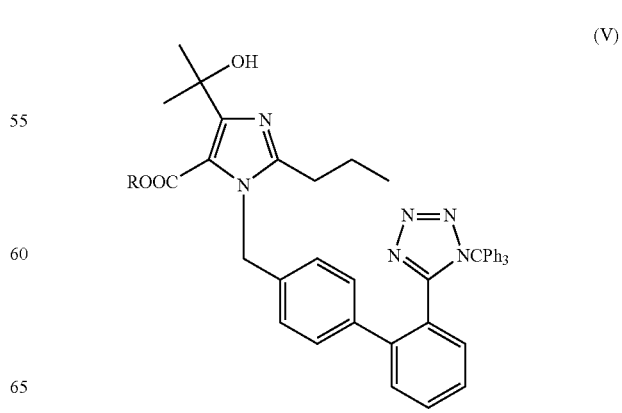

(V)

(b) deesterifying the compound of formula (V) with a base; and (c) reacting the product of step (b) with 4-halomethyl-5-methyl-2-oxo-1,3-dioxolene of formula (IV),

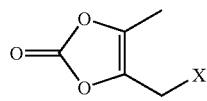
(IV)

wherein X is halogen selected from F or Cl or Br or I, to obtain trityl olmesartan medoxomil of formula (VI), wherein the products of steps (a) and (b) are not isolated and steps (a), (b) and (c) are carried out in a single reaction vessel.

2. The process according to claim 1, wherein R is $C_1$-$C_6$ alkyl.

3. The process according to claim 1, wherein R is ethyl.

4. The process according to claim 1, wherein said polar aprotic solvent in step (a) is selected from the group consisting of acetone, tetrahydrofuran, methyl ethyl ketone, acetonitrile, ethyl acetate, dimethyl formamide, dimethyl acetamide, dimethyl sulfoxide and mixtures thereof.

5. The process according to claim 1, wherein the polar aprotic solvent is dimethyl acetamide.

6. The process according to claim 1, wherein the alkali metal carbonate is potassium carbonate.

7. The process according to claim 1, wherein the alkali metal hydroxide is sodium hydroxide or potassium hydroxide.

8. The process according to claim 1, wherein step (a) is carried out at a temperature ranging from 40° C. to 55° C.

9. The process according to claim 1, wherein step (a) is carried out at a temperature ranging from 40° C. to 50° C.

10. The process according to claim 1, wherein step (a) is carried out at a temperature ranging from 45° C. to 50° C.

11. The process according to claim 1, wherein the base used in step (b) is selected from the group consisting of inorganic bases and organic bases.

12. The process according to claim 11, wherein the inorganic base is selected from the group consisting of alkali metal hydroxides, alkali metal carbonates and alkali metal alkoxides.

13. The process according to claim 11, wherein the organic base is a tertiary amine.

14. The process according to claim 1, further comprising neutralizing the reaction mass of step (c) with an acid selected from the group consisting of carboxylic acids and inorganic acids.

15. The process according to claim 14, wherein the carboxylic acid is formic acid or acetic acid.

16. The process according to claim 14, wherein the inorganic acid is hydrochloric acid, hydrobromic acid or sulfuric acid.

17. A process for the preparation of olmesartan medoxomil of formula (I):

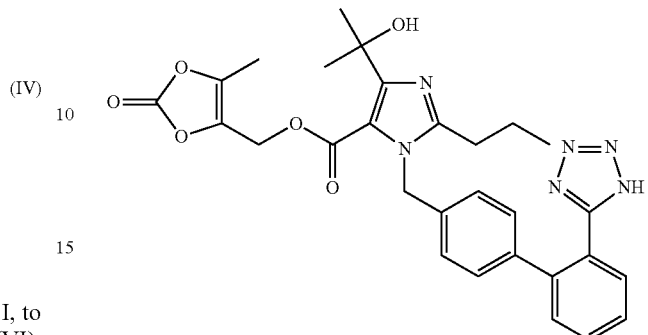
Formula (I)

comprising (a) condensing 4-(1-hydroxy-1-methylethyl)-2-propyl-imidazol-5-carboxylic acid alkyl ester of formula (II):

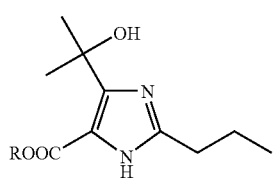
(II)

wherein R is $C_1$-$C_6$ alkyl with trityl biphenyl bromide of formula (III):

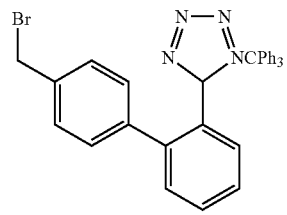
(III)

in the presence of a polar aprotic solvent and a base selected from the group consisting of alkali metal carbonates, alkali metal hydroxides, alkali metal alkoxides, and tertiary amines to obtain a compound of formula (V),

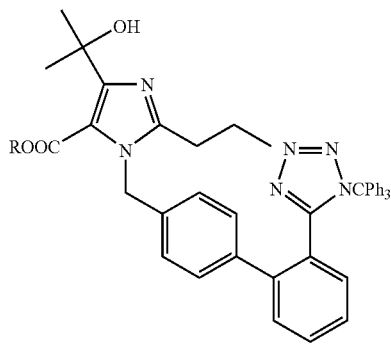
(V)

(b) deesterifying the compound of formula (V) with a base;
(c) reacting the product of step (b) with 4-halomethyl-5-methyl-2-oxo-1,3-dioxolene of formula (IV),

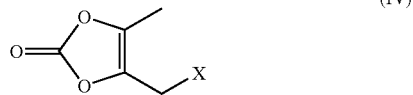

(IV)

wherein X is halogen selected from F or Cl or Br or I, to obtain trityl olmesartan medoxomil of formula (VI);

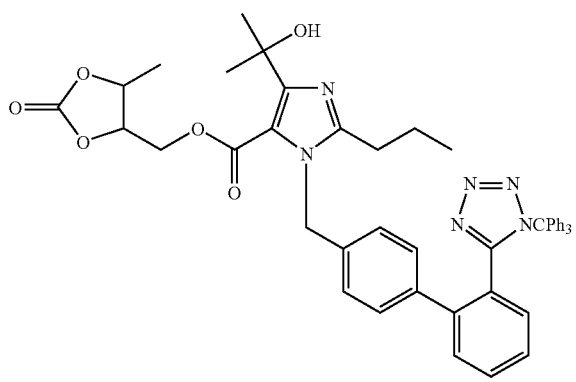

(VI)

and (d) deprotecting the trityl olmesartan medoxomil (VI) to yield olmesartan medoxomil of formula (I), wherein the products of steps (a) and (b) are not isolated and steps (a), (b) and (c) are carried out in a single reaction vessel.

18. The process according to claim 17, wherein steps (a), (b), (c), and (d) are carried out in a single reaction vessel.

19. The process according to claim 17, wherein the trityl olmesartan medoxomil of formula (VI) is isolated prior to deprotection in step (d).

20. The process according to claim 19, wherein the trityl olmesartan medoxomil of formula (VI) is purified prior to deprotection in step (d).

21. The process according to claim 17, wherein the products of steps (a), (b) and (c) are not isolated.

22. The process according to claim 17, wherein the deprotection is carried out in the presence of an acid selected from the group consisting of organic carboxylic acids, sulfonic acids, and inorganic acids.

23. The process according to claim 22, wherein the organic carboxylic acid is formic acid, oxalic acid, acetic acid, trimethyl acetic acid or trifluoroacetic acid.

24. The process according to claim 22, wherein the organic carboxylic acid is acetic acid.

25. The process according to claim 22, wherein the sulfonic acid is methanesulfonic acid or p-toluene sulfonic acid.

26. The process according to claim 22, wherein the inorganic acid is hydrochloric acid, hydrobromic acid, sulfuric acid, pivalic acid or phosphoric acid.

27. The process according to claim 22, wherein the inorganic acid is hydrochloric acid.

28. The process according to claim 1, wherein the process is carried out in a single solvent.

* * * * *

UNITED STATES PATENT AND TRADEMARK OFFICE
CERTIFICATE OF CORRECTION

PATENT NO. : 8,076,492 B2
APPLICATION NO. : 12/444502
DATED : December 13, 2011
INVENTOR(S) : Srinivas Laxminarayan Pathi et al.

It is certified that error appears in the above-identified patent and that said Letters Patent is hereby corrected as shown below:

In the Claims:

Column 16, Lines 5-20, replace " 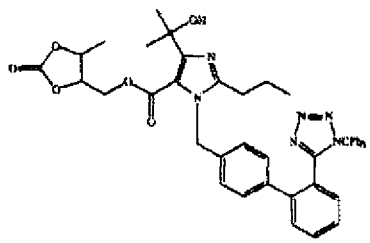 " with

-- 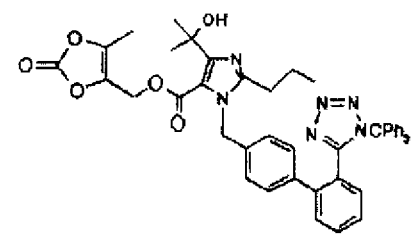

(VI) --.

Signed and Sealed this
Second Day of September, 2014

Michelle K. Lee
*Deputy Director of the United States Patent and Trademark Office*

Column 19, Lines 15-30, replace " 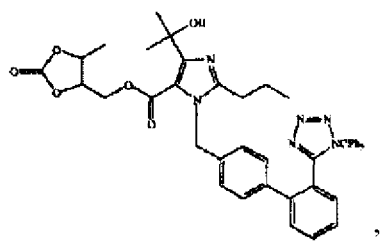 " with
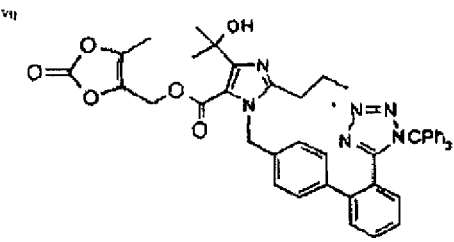
-- (VI) --.